(12) United States Patent
Sasaki et al.

(10) Patent No.: US 10,335,362 B2
(45) Date of Patent: Jul. 2, 2019

(54) WATER-IN-OIL TYPE EMULSION COSMETIC

(75) Inventors: Kazutaka Sasaki, Kanagawa (JP);
Takayuki Omura, Kanagawa (JP);
Masaki Kitajima, Kanagawa (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 609 days.

(21) Appl. No.: 13/812,634

(22) PCT Filed: Oct. 5, 2011

(86) PCT No.: PCT/JP2011/072959
§ 371 (c)(1),
(2), (4) Date: Feb. 15, 2013

(87) PCT Pub. No.: WO2012/050024
PCT Pub. Date: Apr. 19, 2012

(65) Prior Publication Data
US 2014/0148516 A1 May 29, 2014

(30) Foreign Application Priority Data

Oct. 12, 2010 (JP) .................. 2010-229982
Oct. 3, 2011 (JP) .................. 2011-219463

(51) Int. Cl.
*A61K 8/92* (2006.01)
*A61K 8/26* (2006.01)
*A61K 8/31* (2006.01)
*A61K 8/37* (2006.01)
*A61K 8/39* (2006.01)
*A61K 8/86* (2006.01)
*A61K 8/06* (2006.01)
*A61K 8/41* (2006.01)
*A61K 8/49* (2006.01)
*A61K 8/25* (2006.01)
*A61Q 17/04* (2006.01)
*A61Q 19/00* (2006.01)
*A61Q 90/00* (2009.01)

(52) U.S. Cl.
CPC ............... *A61K 8/92* (2013.01); *A61K 8/064* (2013.01); *A61K 8/25* (2013.01); *A61K 8/26* (2013.01); *A61K 8/31* (2013.01); *A61K 8/315* (2013.01); *A61K 8/37* (2013.01); *A61K 8/375* (2013.01); *A61K 8/39* (2013.01); *A61K 8/416* (2013.01); *A61K 8/4973* (2013.01); *A61K 8/86* (2013.01); *A61Q 17/04* (2013.01); *A61Q 19/00* (2013.01); *A61Q 90/00* (2013.01); *A61K 2800/34* (2013.01)

(58) Field of Classification Search
None
See application file for complete search history.

(56) References Cited

U.S. PATENT DOCUMENTS

| 4,164,564 A * | 8/1979 | Chen .................. A61K 8/042 424/62 |
| 5,879,667 A * | 3/1999 | Hanna et al. ............... 424/70.7 |
| 6,204,227 B1 | 3/2001 | Rao et al. |
| 8,815,958 B2 * | 8/2014 | Sasaki .................. A61K 8/064 424/401 |
| 2003/0031642 A1 * | 2/2003 | Lezer ...................... 424/70.12 |
| 2010/0111884 A1 * | 5/2010 | Acker ................. A61K 8/046 424/60 |

FOREIGN PATENT DOCUMENTS

| EP | 0 856 306 | 8/1998 | |
| EP | 0 856 307 | 8/1998 | |
| EP | 0856306 A2 * | 8/1998 | ............... A61K 8/06 |
| EP | 0856306 A2 * | 8/1998 | ............... A61K 8/06 |
| EP | 0856307 A2 * | 8/1998 | ............... A61K 8/06 |
| EP | 0856306 A3 * | 12/1999 | ............... A61K 8/06 |
| JP | 61-245836 | 1/1986 | |
| JP | 61245836 | 11/1986 | |
| JP | 11005714 | 1/1999 | |
| JP | A H11-5714 | 1/1999 | |
| JP | 11-5713 | 12/1999 | |
| JP | 2000-308820 | 7/2000 | |
| JP | 2000-308820 | 11/2000 | |
| JP | 2000308820 | 11/2000 | |

(Continued)

OTHER PUBLICATIONS

JP H11-5714, translation provided by Applicant (Jan. 2013), 18 pages.*

(Continued)

*Primary Examiner* — Bethany P Barham
*Assistant Examiner* — Miriam A Levin
(74) *Attorney, Agent, or Firm* — Andrew F. Young, Esq.; Lackenbach Siegel, LLP

(57) ABSTRACT

The purpose of the present invention is to provide a water-in-oil type cosmetic which ensures emulsion stability in the case where a volatile hydrocarbon oil component is added, has excellent texture such as not leaving a greasy feeling, and is highly compatible with the skin. The present invention relates to a water-in-oil type emulsified cosmetic comprising:

(A) 20 to 30 mass % of an oil component;
(B) a fatty acid ester having an HLB of 5 to 10;
(C) a nonionic surfactant having an HLB of 1 to 4;
(D) an organic modified clay mineral; and
(E) water, wherein volatile hydrocarbon oil accounts for 10 mass % or more of the oil component (A) and silicone oil is not contained.

4 Claims, No Drawings

(56) References Cited

FOREIGN PATENT DOCUMENTS

| JP | 2001131421 | 5/2001 |
|---|---|---|
| JP | 2001199846 | 7/2001 |
| JP | 2004-67628 | 4/2004 |
| JP | 2005232068 | 9/2005 |
| JP | 2005-320263 | 11/2005 |
| JP | 2008-208045 | 9/2008 |
| JP | 2008208045 | 9/2008 |
| JP | 2009-40738 | 2/2009 |
| JP | 2010-229982 | 10/2010 |
| JP | 2011-219463 | 10/2011 |
| JP | 2011-219563 | 10/2011 |
| RU | 2013119153/15 | 10/2011 |
| WO | PCT/JP2011/072959 | 10/2011 |
| WO | PCT/JP 2011/072959 | 10/2011 |

OTHER PUBLICATIONS

JP 2005/320263 A ("JP263") (machine translation from AIPO, USPTO, Mar. 9, 2015; 26 pages).*
Omura, JP2005-320263, manual translation by Dr. Tetsuo Nakatsu (Jul. 23, 2015), 35 pages.*
The Herbarie, Emulsifiers with HLB Values, [Retrieved from internet <URL: http://www.theherbarie.com/files/resource-center/formulating/Emulsifiers_HLB_Values.pdf >], [Downloaded Oct. 30, 2017], 3 pages (Year: 2017).*
Philip Haw, Uniqema; The HLB System, A Time Saving Guide to Surfactant Selection, Presentation to the Midwest Chapter of the Society of Cosmetic Chemists (citation continued below) (Year: 2004).*
Philip Haw (citation continued from above) (Mar. 9, 2004), [Retrieved from internet <URL: http://www.lotioncrafter.com/pdf/The_HLB_System.pdf (Year: 2004).*
International Preliminary Report on Patentability, PCT/JP2011/072959, dated May 8, 2013, 6 pages. (English translation) (Year: 2013).*
International Preliminary Report on Patentability, PCT/JP2011/072959, dated May 8, 2013, 5 pages. (Japanese with cover page in English) (Year: 2013).*
Espacenet, Bibliographic data, WO-2012/050024 A1 (publication of application WO2011JP72959), 2 pages (Year: 2012).*
ICI Americas Inc., "The HLB System: a time-saving guide to emulsifier selection" (1984) (22 pages) (Year: 1984).*
Society of Cosmetic Chemists, The HLB system, [Retrieved from internet <URL: http://caliscc.org/images/presentations/Mentor_2015_HLB.pdf >], [Downloaded Apr. 24, 2019], (30 pages + 1 page citation information) (Year: 2019).*
International Search Report for PCT/JP2011/072959, dated Dec. 20, 2011, English 2 pgs and JP 2 pgs.
JP 2011-219463, Notification of Reasons for Refusal dated Dec. 9, 2011, 2 pages—Japanese, 3 pages—English.
JP 2011-219463, Response to Office Action dated Jul. 23, 2012, 3 pages—Japanese, 4 pages—English.
Evonik Industries, ABIL® WE 09 Emulsifier for the formulations of W/O creams and lotions, pp. 4-8,—English, Evonik Goldschmidt GmbH, personal-care@evonik.com, www.evonik.com/personal-care, dated.
Polysorbate 20, Wikipedia, http://en.wikipedia.org/wiki/Polysorbate_20, 3 pages dated Feb. 2, 2012.
JP 2011-219463, JPO Amendment dated Feb. 7, 2011, 2 pages—Japanese, 2 pages—English.
Office Action for RU 2013119153/15, dated Sep. 16, 2015, English 4 pgs and Russian—4 pgs.
European Search Report, 11832459.9 (PCT/JP 2011072959), dated Aug. 7, 2015, 8 pages—English.
Japanese Appln. No. 2013/7004585, Korean Office Action dated Jun. 23, 2017, 10 pages—Japanese, 5 pages—English.

* cited by examiner

WATER-IN-OIL TYPE EMULSION COSMETIC

CROSS REFERENCE TO RELATED APPLICATIONS

This application claims priority to International Ser. No. PCT/JP2011/072959 filed Oct. 5, 2011, the entire contents of which are incorporated herein fully by reference, which in turn claims priority to JP Ser. No. JP 2010-229982, filed on Oct. 12, 2010 and JP Ser. No. JP 2011-219463, filed on Mar. 10, 2011.

TECHNICAL FIELD

The present invention relates to a water-in-oil type emulsified cosmetic which is excellent in stability, does not leave a greasy feeling, and is highly compatible with the skin.

BACKGROUND ART

A water-in-oil type cosmetic has heretofore been used as a skin cosmetic such as a sunscreen cosmetic which is required to have waterproofness. However, since a water-in-oil type emulsion inevitably contains a relatively large amount of an oil component, the emulsion has a problem in texture such as leaving a greasy feeling when applied onto the skin.

Though a volatile oil component is blended in order to improve the greasy feeling of the water-in-oil type emulsion, an emulsion which mainly contains volatile silicone oil as the volatile oil component has marked slippery feel and squeakiness and sometimes impairs appropriate moisturized feeling after application. Further, even though the slippery feel and squeakiness are improved when a volatile hydrocarbon oil component is incorporated into the water-in-oil type emulsion containing the nonvolatile silicone oil, such emulsion has a problem of deterioration in long term stability.

Patent Document 1 describes a transfer resistant cosmetic composition containing a nonvolatile silicone compound and a nonvolatile hydrocarbon oil component which is incompatible with the silicone. The cosmetic contains a volatile hydrocarbon oil component (solvent) in which the nonvolatile hydrocarbon oil component is soluble and the nonvolatile silicone compound is soluble or dispersible. The cosmetic is improved in transfer resistance by specifying a dissolution parameter of the nonvolatile hydrocarbon oil component.

Patent Document 2 describes a water-in-oil type emulsion composition obtained by incorporating a fiber, a silicone surfactant, and clay, which allegedly has good stability at a high temperature (e.g. 45° C.)

Patent Document 3 describes a water-in-oil type emulsified sunscreen cosmetic containing a zinc oxide powder subjected to a special surface hydrophobizing treatment, volatile silicone, polyoxyalkylene-modified organopolysiloxane, and water. It is described that the water-in-oil type emulsified cosmetic may further contain an organic modified clay mineral, and that an emulsion which stably incorporates the powder can be obtained without increasing an oil component such as nonvolatile silicone.

However, in the conventional techniques including Patent Documents 1 to 3, the problem of impairment of stability of emulsion, which can occur when volatile hydrocarbon oil is incorporated into a water-in-oil type emulsion, is not recognized at all, and any countermeasure for the problem is not disclosed nor suggested. Further, a problem of deterioration of compatibleness with the skin caused by incorporation of a silicone oil component has been raised.

CITATION LIST

Patent Document

Patent Document 1: Japanese Patent Application Laid-Open (JP-A) No. 2001-199846
Patent Document 2: JP-A No. 2001-131421
Patent Document 3: JP-A No. 2005-232068

SUMMARY OF INVENTION

Problem to be Solved by the Invention

Accordingly, an object of the present invention is to provide a water-in-oil type cosmetic which ensures emulsion stability in the case where a volatile hydrocarbon oil component is added, has excellent texture such as not leaving a greasy feeling, and is highly compatible with the skin.

The inventors conducted extensive researches in the aim of attaining the above-described object to find that it is possible to obtain a cosmetic which is stable, is excellent in texture, and is highly compatible with the skin by combining a fatty acid ester having an HLB within a predetermined range, a nonionic surfactant having an HLB within a predetermined range, and an organic modified clay mineral even in the case where volatile hydrocarbon oil is 10 mass % or 20 mass % or more of an oil component, thereby accomplishing the present invention.

Solution to Problem

More specifically, the present invention provides a water-in-oil type emulsified cosmetic containing:
(A) 20 to 30 mass % of an oil component;
(B) a fatty acid ester having an HLB of 5 to 10;
(C) a nonionic surfactant having an HLB of 1 to 4;
(D) an organic modified clay mineral; and
(E) water,
wherein volatile hydrocarbon oil accounts for 10 mass % or more of the oil component (A) and silicone oil is not contained.

Advantageous Effects of Invention

Since a skin cosmetic according to the present invention contains a volatile hydrocarbon oil component, the skin cosmetic does not leave a greasy feeling, does not has slippery feel and squeakiness, is excellent in texture, is highly compatible with the skin, and imparts a moist feeling to the skin after application. Further, the emulsion has excellent long-term stability.

DESCRIPTION OF EMBODIMENTS

An emulsified cosmetic of the present invention contains an oil component (component A) as an essential component. The oil component used in the present invention is not particularly limited insofar as the oil component is a liquid oil component which has heretofore been used for a cosmetic and the like and may appropriately be selected from among natural or synthetic hydrocarbon oil, higher fatty acids, higher alcohols, ester oil, and the like to be used. However, from the viewpoint of improvement in compatibility with the skin, the emulsified cosmetic of the present invention does not contain silicone oil.

A content of the oil component in the cosmetic of the present invention may be 20 to 30 mass %. Further, the present invention is characterized in that a volatile hydrocarbon oil component accounts for 10 mass % or more of the oil component, more preferably 20 mass % or more of the oil component. High compatibility with the skin is attained in the cosmetic of the present invention by incorporating the volatile oil component in the above-specified predetermined amount or more.

The volatile hydrocarbon oil component to be incorporated into the cosmetic of the present invention is not particularly limited insofar as the volatile hydrocarbon oil component is hydrocarbon oil which has heretofore been used for a cosmetic and the like and has volatility at a room temperature, and examples thereof include isododecane, isohexadecane, hydrogenated polyisobutene, and the like.

The emulsified cosmetic of the present invention contains a fatty acid ester (component B) having an HLB of 5 to 10. The fatty acid ester (HLB=5 to 10) to be used in the present invention may be one kind or two or more kinds appropriately selected from among those ordinarily used for a cosmetic and the like.

Specific examples thereof include the following.

Polyglycerin fatty acid ester such as hexaglyceryl monostearate (HLB 9.0), hexaglyceryl monooleate (HLB 9.0), decaglyceryl distearate (HLB 9.5), and decaglyceryl diisostearate (HLB 10.0). Polyoxyethylene glycerin fatty acid ester such as polyoxyethylene (hereinafter abbreviated to POE) (5) glyceryl monostearate (HLB 9.5), and POE (5) glyceryl monooleate (HLB 9.5). Polyoxyethylene sorbitan fatty acid ester such as POE (6) sorbitan monostearate (HLB 9.5) and POE (6) sorbitan monooleate (HLB 10.0). Polyethylene glycol fatty acid ester such as PEG-8 diisostearate (HLB 6.0), PEG-12 diisostearate (HLB 8.0), PEG-8 isostearate (HLB 10.0), and PEG-8 dioleate (HLB 8.0). Polyoxyethylene glyceryl isostearate such as PEG-10 glyceryl triisostearate (HLB 5.0), PEG-8 glyceryl isostearate (HLB 10.0), and PEG-10 glyceryl isostearate (HLB 10.0).

A content of the fatty acid ester having HLB of 5 to 10 (component B) in the cosmetic of the present invention may be 0.01 to 2 mass %, preferably 0.01 to 1 mass %. The long-term stability of a preparation is deteriorated when the content is less than 0.1 mass %, and it is difficult to obtain a preparation as a water-in-oil emulsion when the content exceeds 2 mass % because the emulsifiability becomes worse.

The emulsified cosmetic of the present invention contains a nonionic surfactant having HLB of 1 to 4 (component C). The nonionic surfactant (HLB=1 to 4) to be used in the present invention may be one kind or two or more kinds appropriately selected from among those ordinarily used for a cosmetic and the like.

For example, examples of a hydrocarbon-based surfactant include glyceryl diisostearate (HLB 3.0), PEG-4 sorbitan triisostearate (HLB 3.0), POE (2) stearyl ether (HLB 4.0), self-emulsification type propylene glycol monostearate (HLB 4.0), glyceryl myristate (HLB 3.5), glyceryl monostearate (HLB 4.0), self-emulsification type glyceryl monostearate (HLB 4.0), glyceryl monoisostearate (HLB 4.0), glyceryl monooleate (HLB 2.5), hexaglyceryl tristearate (HLB 2.5), decaglyceryl pentastearate (HLB 3.5), decaglyceryl pentaisostearate (HLB 3.5), decaglycerylpentaoleate (HLB 3.5), sorbitan tristearate (HLB 2.1), POE (6) sorbitol hexastearate (HLB 3.0), POE (3) castor oil (HLB 3.0), PEG (2) monostearate (HLB 4.0), ethylene glycol monostearate (HLB 3.5), and the like.

Examples of a silicone-based surfactant include PEG-9 polydimethylsiloxyethyl dimethicone (HLB 3.8), lauryl PEG-9 polydimethylsiloxy dimethicone (HLB 2.8), and the like. For example, a polyoxyethylene polydimethylsiloxyethyl dimethicone copolymer (also described as "PEG-9 polydimethylsiloxyethyl dimethicone") described as polyoxyalkylene-modified organopolysiloxane in Patent Document 3 is commercially available as Silicone KF-6028 (manufactured by Shin-Etsu Chemical Co., Ltd.), and the commercially available product may also be used.

A content of the nonionic surfactant having HLB of 1 to 4 in the cosmetic of the present invention may be 0.1 to 5 mass %, preferably 0.1 to 3 mass %. It is difficult to attain the excellent emulsion stability when the content is less than 0.1 mass %, while texture is deteriorated in some cases when the content exceeds 5 mass %.

The organic modified clay mineral (component D) to be incorporated into the emulsified cosmetic of the present invention is used as a coemulsifier and it is preferable to use those obtained by modifying a clay mineral with a quaternary ammonium salt type cationic surfactant, wherein the clay mineral is one kind of colloidal water-containing aluminum silicate having a three-layer structure and generally represented by the following formula:

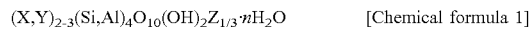 [Chemical formula 1]

(wherein X=Al, Fe(III), Mn(III), or Cr(III); Y=Mg, Fe(II), Ni, Zn, or Li; Z=K, Na, or Ca).

Specifically, the organic modified clay mineral is obtainable by treating the clay mineral such as natural or synthetic (in this case, the (OH) group in the formula is substituted by fluorine) montmorillonites including montmorillonite, saponite, hectorite, and the like (examples of a commercialized product thereof include Veegum, Kunipia, Laponite, and the like) and synthetic mica known as sodium silicic mica, sodium or lithium taeniolite (examples of a commercialized product thereof include Dimonite manufactured by Topy Industries, Limited) with the quaternary ammonium salt type cationic surfactant.

The quaternary ammonium salt type cationic surfactant used herein is represented by the following general formula:

[Chemical formula 2]

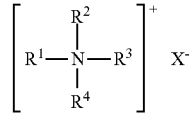

(wherein $R^1$ represents an alkyl group or a benzyl group having 10 to 22 carbon atoms; $R^2$ represents a methyl group or an alkyl group having 10 to 22 carbon atoms; each of $R^3$ and $R^4$ is an alkyl group or a hydroxylalkyl group having 1 to 3 carbon atoms; and X represents a halogen atom or a methyl sulfate residue).

Examples of the quaternary ammonium salt type cationic surfactant include dodecyltrimethylammonium chloride, myristyltrimethylammonium chloride, cetyltrimethylammonium chloride, stearyltrimethylammonium chloride, arachyltrimethylammonium chloride, behenyltrimethylammonium chloride, myristyldimethylethylammonium chloride, cetyldimethylethylammonium chloride, stearyldimethylethylammonium chloride, arachyldimethylethylammonium chloride, behenyldimethylethylammonium chloride, myristyldiethylmethylammonium chloride, cetyldiethylmethylammonium chloride, stearyldiethylmethylammonium chloride, arachyldiethylmethylammonium chloride, behenyldiethylmethylammonium chloride, benzyldimethylmyristylammonium chloride, benzyldimethylcetylammonium chloride, benzyldimethylstearylammonium chloride, benzyldimethylbehenylammonium chloride, benzylmethylethylcetylammonium chloride, benzylmethylethylstearylammonium chloride, dibehenyldihydroxyethylammonium chloride, and corresponding bromides and the like, and further dipalmitylpropylethylammonium methylsulfate, and the like. When carrying out the present invention, one kind or two or more kinds of the above are arbitrarily selected.

Typical examples of the organic modified clay mineral include dimethyldistearylammonium hectorite, benzyldimethylstearylammonium hectorite, distearyldimethylammonium chloride-treated aluminum magnesium silicate, and the like. Examples of commercialized products thereof include Bentone 27 (benzyldimethylstearylammonium hectorite manufactured by Elementis Specialties) and Bentone 38 (distearyldimethylammonium chloride-treated hectorite manufactured by Elementis Specialties).

A content of the organic modified clay mineral (component D) in the cosmetic of the present invention may be 1 to 20 mass %, preferably 1 to 10 mass %. It is difficult to attain the excellent emulsion stability and favorable viscosity when the content is less than 1 mass %, while there is a tendency that mealy feeling occurs when the content exceeds 20 mass %.

The emulsified cosmetic of the present invention contains the above-described components A to D and water (component E) as essential components, and other components which are ordinarily incorporated into skin cosmetics may be incorporated within a range which does not inhibit the effect of the present invention. More specifically, a powder, a lipid soluble UV absorber, a water soluble UV absorber, a sequestering agent, a neutralizer, a pH adjuster, an antioxidant, an antibacterial agent, various drugs, various extracts, and the like may be included.

The skin cosmetic of the present invention is capable of eliminating the greasy feeling and of imparting high compatibility with the skin and a moist feeling owing to the incorporation of the volatile hydrocarbon. Further, the skin cosmetic is excellent in emulsion stability owing to the combination of the surfactants (components B and C) each having the predetermined HLB. Therefore, the skin cosmetic is suitably used as a skin cosmetic for the usages for which water-in-oil type emulsions have heretofore been used.

Examples

The present invention will hereinafter be described in more details in conjunction with examples, but the present invention is not limited to the following Examples. Further, each of contents in the following Examples and the like indicates mass % unless otherwise noted.

Water-in-oil type emulsion compositions (Examples) of the present invention and compositions of Comparative Examples were prepared and evaluated on the following items.

1. Emulsion Particle Stability

The emulsion was frozen and then evaluated by visual observation.

○: Emulsion particles were uniformly dispersed.

X: Particle coalescence was observed.

2. Appearance Stability

An appearance of the prepared emulsion after being left to stand for 4 weeks at a room temperature was evaluated.

○: Separation was observed.

X: Stable without separation.

3. Compatibility with the Skin

Each of the prepared samples was used by female panel of experts (N=7) for evaluation of compatibility with the skin.

○: 6 or more panelists rated high compatibility with the skin.

Δ: 4 to 5 panelists rated high compatibility with the skin.

X: 3 or less panelists rated high compatibility with the skin.

Samples of the compositions listed in the following Tables I to 4 were prepared and evaluated on the same items. Results of the evaluation are also shown in the Tables.

TABLE 1

|  | Comparative Example 1 | Example 1 |
|---|---|---|
| Water | Balance | Balance |
| Glycerin | 13 | 13 |
| 1,3-butylene glycol | 2 | 2 |
| Dimethyldistearylammonium hectorite | 2.0 | 2.0 |
| PEG-9 polydimethylsiloxyethyl dimethicone (HLB = 3.8) | 1.3 | 1.3 |
| PEG-8 diisostearate (HLB = 6) | 0.5 | 0.5 |
| Liquid paraffin | 2.5 | 2.5 |
| Isohexadecane | — | 9 |
| Isododecane | — | 8 |
| Vaseline | 1 | 1 |
| Dimethicone | 17 | — |
| Cetyl ethylhexanoate | 5 | 5 |
| Phenoxyethanol | 0.5 | 0.5 |
| Compatibility with the skin | X | ○ |
| Emulsion particle stability | ○ | ○ |
| Appearance stability | ○ | ○ |

Example 1 in which the silicone oil component (dimethicone) used in Comparative Example 1 was replaced by the volatile hydrocarbon oil (isohexadecane and isododecane) was free from the unsatisfactory compatibility with the skin observed in Comparative Example 1 and attained high compatibility with the skin.

TABLE 2

|  | Comparative Example 2 | Comparative Example 3 | Example 2 | Example 3 | Example 4 | Example 5 | Example 6 |
|---|---|---|---|---|---|---|---|
| Water | Balance | Balance | Balance | Balance | Balance | Balance | Balance |
| Glycerin | 13 | 13 | 13 | 13 | 13 | 13 | 13 |
| 1,3-butylene glycol | 2 | 2 | 2 | 2 | 2 | 2 | 2 |
| Dimethyldistearylammonium hectorite | 2.0 | 2.0 | 2.0 | 2.0 | 2.0 | 2.0 | 2.0 |
| PEG-9 polydimethylsiloxyethyl dimethicone (HLB = 3.8) | 2.1 | — | 1.3 | 1.3 | 1.3 | 1.3 | 1.3 |

TABLE 2-continued

| | Comparative Example 2 | Comparative Example 3 | Example 2 | Example 3 | Example 4 | Example 5 | Example 6 |
|---|---|---|---|---|---|---|---|
| PEG-8 diisostearate (HLB = 6) | — | 1 | 0.5 | — | — | — | — |
| PEG-12 diisostearate (HLB = 8) | — | — | — | 0.5 | — | — | — |
| PEG-8 isostearate (HLB = 10) | — | — | — | — | 0.5 | — | — |
| PEG-8 dioleate (HLB = 6) | — | — | — | — | — | 0.5 | — |
| PEG-10 glyceryl triisostearate (HLB = 5) | — | — | — | — | — | — | 0.5 |
| Liquid paraffin | 2.5 | 2.5 | 2.5 | 2.5 | 2.5 | 2.5 | 2.5 |
| Isohexadecane | 9 | 9 | 9 | 9 | 9 | 9 | 9 |
| Isododecane | 8 | 8 | 8 | 8 | 8 | 8 | 8 |
| Vaseline | 1 | 1 | 1 | 1 | 1 | 1 | 1 |
| Cetyl ethylhexanoate | 5 | 5 | 5 | 5 | 5 | 5 | 5 |
| Phenoxyethanol | 0.5 | 0.5 | 0.5 | 0.5 | 0.5 | 0.5 | 0.5 |
| Compatibility with the skin | (—) | (—) | ○ | ○ | ○ | ○ | ○ |
| Emulsion particle stability | X | X | ○ | ○ | ○ | ○ | ○ |
| Appearance stability | X | X | ○ | ○ | ○ | ○ | ○ |

TABLE 3

| | Example 7 | Example 8 | Example 9 |
|---|---|---|---|
| Ion exchange water | Balance | Balance | Balance |
| Glycerin | 13 | 13 | 13 |
| 1,3-butylene glycol | 2 | 2 | 2 |
| Dimethyldistearylammonium hectorite | 2.0 | 2.0 | 2.0 |
| PEG-8 diisostearate (HLB = 6) | 0.5 | 0.5 | 0.5 |
| Diglyceryl diisostearate (HLB = 3) | 1.3 | — | — |
| PEG-4 sorbitan triisostearate (HLB = 3) | — | 1.3 | — |
| Lauryl PEG-9 polydimethylsiloxy dimethicone (HLB = 2.8) | — | — | 1.3 |
| Liquid paraffin | 2.5 | 2.5 | 2.5 |
| Isohexadecane | 13 | 13 | 13 |
| Isododecane | 10 | 10 | 10 |
| Phenoxyethanol | 0.5 | 0.5 | 0.5 |
| Compatibility with the skin | ○ | ○ | ○ |
| Emulsion particle stability | ○ | ○ | ○ |
| Appearance stability | ○ | ○ | ○ |

Comparative Examples 2 and 3 which lacks either one of the fatty acid ester having HLB of 5 to 10 (Component B) and the nonionic surfactant having HLB of 1 to 4 (Component C) failed to give a stable emulsion, and, therefore, it was impossible to evaluate the texture. In contrast, in the case where the HLB value was varied within the predetermined range by variously replacing the component B or the component C (Examples 2 to 9) and in the case where the contents of the components B and C were varied (Examples 10 to 15), it was proved that stable water-in-oil emulsions were prepared and that cosmetics having high compatibility with the skin were able to be obtained.

(Formulation 1)

| Skin Cream | |
|---|---|
| Components | Content (mass %) |
| (1) Isododecane | 5 |
| (2) Isohexadecane | 4 |
| (3) Mineral oil | 5 |

TABLE 4

| | Example 10 | Example 11 | Example 12 | Example 13 | Example 14 | Example 15 |
|---|---|---|---|---|---|---|
| Water | Balance | Balance | Balance | Balance | Balance | Balance |
| Glycerin | 13 | 13 | 13 | 13 | 13 | 13 |
| 1,3-butylene glycol | 2 | 2 | 2 | 2 | 2 | 2 |
| Dimethyldistearylammonium hectorite | 2.0 | 2.0 | 2.0 | 2.0 | 2.0 | 2.0 |
| PEG-9 polydimethylsiloxyethyl dimethicone (HLB = 3.8) | 0.8 | 1.5 | 2 | 3 | 1.5 | 1.5 |
| PEG-8 diisostearate (HLB = 6) | 0.5 | 0.5 | 0.5 | 0.5 | 0.2 | 0.6 |
| Liquid paraffin | 2.5 | 2.5 | 2.5 | 2.5 | 2.5 | 2.5 |
| Isohexadecane | 9 | 9 | 9 | 9 | 9 | 9 |
| Isododecane | 8 | 8 | 8 | 8 | 8 | 8 |
| Vaseline | 1 | 1 | 1 | 1 | 1 | 1 |
| Cetyl ethylhexanoate | 5 | 5 | 5 | 5 | 5 | 5 |
| Phenoxyethanol | 0.5 | 0.5 | 0.5 | 0.5 | 0.5 | 0.5 |
| Compatibility with the skin | ○ | ○ | ○ | ○ | ○ | ○ |
| Emulsion particle stability | ○ | ○ | ○ | ○ | ○ | ○ |
| Appearance stability | ○ | ○ | ○ | ○ | ○ | ○ |

Skin Cream -continued

| Components | Content (mass %) |
|---|---|
| (4) Cetyl ethylhexanoate | 10 |
| (5) Dimethyldistearylammonium hectorite | 2 |
| (6) PEG-8 diisostearate (HLB = 6) | 0.5 |
| (7) Diglyceryl diisostearate (HLB = 3) | 1.3 |
| (8) Glycerin | 13 |
| (9) 1,3-butylene glycol | 2 |
| (10) Phenoxyethanol | 0.5 |
| (11) Water | balance |

Production Method: (1) to (7) were homogeneously mixed and dissolved at a room temperature (oil phase). Meanwhile, (8) to (11) were homogeneously mixed and dissolved at a room temperature (water phase). The oil phase was added to the water phase, and the mixture was emulsified by using a homo mixer to obtain a desired skin cream.

(Formulation 2)

Skin Care Cream

| Components | Content (mass %) |
|---|---|
| (1) Isododecane | 5 |
| (2) Isohexadecane | 10 |
| (3) Vaseline | 2.5 |
| (4) Mineral oil | 5 |
| (5) Dimethyldistearylammonium hectorite | 2 |
| (6) PEG-8 dioleate (HLB = 6) | 0.5 |
| (7) PEG-9 polydimethylsiloxyethyl dimethicone (HLB = 3.8) | 1.3 |
| (8) Glycerin | 13 |
| (9) 1,3-butylene glycol | 2 |
| (10) Tranexamic acid | 2 |
| (11) Vitamin E acetate | 0.5 |
| (12) Potassium 4-methoxysalicylate | 1 |
| (13) Phenoxyethanol | 0.5 |
| (14) Water | balance |

Production Method: (1) to (7) were heated to 50° C. and homogeneously mixed and dissolved (oil phase). Meanwhile, (8) to (14) were homogeneously mixed and dissolved at a room temperature (water phase). The oil phase was added to the water phase, and the mixture was emulsified by using a homo mixer to obtain a desired skin care cream.

(Formulation 3)

Sun Care Cream

| Components | Content (mass %) |
|---|---|
| (1) Isododecane | 8 |
| (2) Isohexadecane | 9 |
| (3) Octylmethoxy cinnamate | 6 |
| (4) Octocrylene | 5 |
| (5) Dimethyldistearylammonium hectorite | 2 |
| (6) PEG-8 diisostearate (HLB = 6) | 0.5 |
| (7) PEG-4 sorbitan triisostearate (HLB = 3) | 1.3 |
| (8) Glycerin | 13 |
| (9) 1,3-butylene glycol | 2 |
| (10) Phenoxyethanol | 0.5 |
| (11) Water | balance |

Production Method: (1) to (7) were homogeneously mixed and dissolved at a room temperature (oil phase). Meanwhile, (8) to (11) were homogeneously mixed and dissolved at a room temperature (water phase). The oil phase was added to the water phase, and the mixture was emulsified by using a homo mixer to obtain a desired sun care cream.

The invention claimed is:

1. A water-in-oil type emulsified cosmetic consisting essentially of:
    (A) 20 to 30 mass % of an oil component, the oil component comprising:
        (i) at least 10 mass % or more with respect to the oil component of a volatile hydrocarbon oil, and
        (ii) no silicone oil;
    (B) at least one fatty acid ester selected from the group consisting of PEG-8 diisostearate, PEG-12 diisostearate, PEG-8 dioleate, and PEG-10 glyceryl triisostearate;
    (C) 0.1 to 3 mass % of at least one nonionic surfactant selected from the group consisting of glyceryl diisostearate, PEG-4 sorbitan triisostearate, PEG-9 polydimethylsiloxyethyl dimethicone and lauryl PEG-9 polydimethylsiloxy dimethicone;
    (D) an organic modified clay mineral; and
    (E) water,
    wherein said volatile hydrocarbon oil is selected from the group consisting of isododecane, isohexadecane, hydrogenated polyisobutene and mixtures thereof.

2. The cosmetic according to claim 1, wherein said 20 to 30 mass % of an oil component comprises 20% or more by mass of said volatile hydrocarbon oil.

3. The cosmetic according to claim 1, wherein the water is present at 55.2 to 78.8 mass % relative to the total mass of the cosmetic.

4. The cosmetic according to claim 3, wherein said 20 to 30 mass % of an oil component comprises 20% or more by mass of said volatile hydrocarbon oil.

* * * * *